United States Patent [19]

Cheney et al.

[11] Patent Number: 5,426,040
[45] Date of Patent: Jun. 20, 1995

[54] METHODS FOR PRODUCING IMPROVED STRAINS OF SEAWEED BY FUSION OF SPORE-PROTOPLASTS, AND RESULTANT SEAWEEDS AND PHYCOCOLLOIDS

[75] Inventors: Donald P. Cheney, Wakefield, Mass.; Clifford Duke, Pawtucket, R.I.

[73] Assignee: Northeastern University, Boston, Mass.

[21] Appl. No.: 126,092

[22] Filed: Sep. 23, 1993

Related U.S. Application Data

[63] Continuation of Ser. No. 815,641, Dec. 30, 1991, abandoned, which is a continuation of Ser. No. 395,445, Aug. 17, 1989, abandoned.

[51] Int. Cl.$^6$ .............................................. C12N 5/26
[52] U.S. Cl. ................................. 435/172.2; 435/101; 435/240.47; 435/946; 800/220; 800/DIG. 7
[58] Field of Search ............ 435/172.2, 240.47, 240.48, 435/946, 257, 101; 47/1.4; 935/91, 94, 98; 800/220, DIG. 7

[56] References Cited

U.S. PATENT DOCUMENTS 4,996,389 2/1991 Bird .................................... 800/200

OTHER PUBLICATIONS

Cheney, Donald P. "Genetic Engineering in Sea Weeds: Applications and Current Status", published in Beihefte zur Nova Hedwigia 83:22–29, 1986.
Cheney, "Genetic Engineering in Sea Weeds: Applications and Current status", published in Bechefte zur Nova Hedwigia 80 (1986), pp. 22–25.
Potrykus (Jun. 1990) Bid/Technilogy 8:535–542.
Fujita et al. (Sep. 20, 1987) Jap. J. Phycol. 35:201–208.
Cheney et al (1986) J. Phycol. 22: 238–243.
Kyozuka et al (1987) Mol Gen. Genet. 206: 408–413.
Shillito et al (Dec. 1905) Bio/Technology 3: 1099–1103.
Zimmermann et al (1981) Planta 151: 26–32.
Kapraun et al (1988) Proceedings of the American Society for Cell Biology, Bethesda, MD.

Cheney (1988) Proceedings of the First Int'l Symposium on Marine Molecular Biology, Baltimore, Md.
Cheney (Apr. 29, 1989), 28th Northeast Algal Symposium, Woods Hole, Mass.
Gusev, et al (1987) Marine Biology 95:593–597.
Pollock et al (1983) Plant Cell Reports 2:36–39.
Butler, et al. (Nov. 1989 Journal of Experimental Botany 40 (220):1237–1246.
Bird, C. J. and J. McLachlin, "Some Underutilized Taxonomic Criteria in Gracilaria (Rhodophyta, Cigartinales)", Botanica Marina, vol. XXV, pp. 557–562, 1982.
Cheney, D., Abstract & Talk, 28th Northeast Algal Symposium, held in Woods Hole, Apr. 29, 1989.
Cheney, Donald P., Abstract & Talk, "Genetic Manipulation of Marine Algae Through Protoplast and Tissue Culture Technology", Third Int'l Phycological Congress, Australia, 1988. Pub. in Congress Proceedings, p. 8.

(List continued on next page.)

*Primary Examiner*—Che S. Chereskin
*Attorney, Agent, or Firm*—Weingarten, Schurgin, Gagnebin & Hayes

[57] ABSTRACT

Methods for producing hybrid and transgenic strains of marine algae, and seaweeds and phycocolloids produced by the product seaweeds. Hybrid marine algae are produced by preparing protoplasts from spores of parental algal plants, fusing the spore-protoplast to form heterokaryon fusion products, isolating selected fusion products, and culturing these to produce multicellular material. Similarly, transgenic marine algae are produced by preparing protoplasts from spores of a marine algal plant, introducing foreign DNA into the resulting spore-protoplasts to form transformed spore-protoplasts, selecting certain transformed spore-protoplasts, and culturing these to produce transgenic multicellular material.

10 Claims, 1 Drawing Sheet

OTHER PUBLICATIONS

Cheney, Donald P., "Genetic Manipulation of Marine Algae Through Protoplast and Tissue Culture Technology", Third Int'l Phycological Congress, Aug. 1988, Melbourne, Australia.

Cheney, Donald P., Emily Mar, Naotsune Saga and John van der Meer, "Protoplast Isolation and Cell Division in the Agar-Producing Seaweed Gracilaria (Rhodophyta)", J. Phycol. 22, 238-243 (1986).

Fujita, Yuji and Seiji Migita, "Fusion of protoplasts form thalli of two different color types in Porphyra yezoensis Ueda and development of fusion products", SORUI, Japanese J. of Phycol, 35, 3, 201-208 (1987).

Kao, K. N. and M. R. Michayluk, "A Method for High-Frequency Intergeneric Fusion of Plant Protoplasts", Planta (Berl.) 115, 335-367 (1974).

Nonomura, Arthur, Michio, "A future of phycotechnology" in Algae and Human Affairs by C. Lembi and J. R. Waaland, Cambridge University Press. 1988.

Pirrie, A and J. B. Power, "The production of fertile, triploid somatic hybrid plants (Nicotiana glutinosa (n)+N. tabacum (2N) via gametic: somatic protoplast fusion" Theor. Appl. Genet. 72, 48-52 (1986).

Plastino, Estela M. and Eurico C. De Oliveira F., "Sterility Barriers among Species of Gracilaria (Rhodophyta, Gigartinales) from the Sao Paulo Littoral, Brazil", Br. phycol. J. 23, 267-271 (1988).

Power, J. B., M. R. Davey, J. P. Freeman, B. J. Mulligan, and E. C. Cocking, "Fusion and Transformation of Plant Protoplasts" in Methods in Enzymology, vol. 118, Academic Press, Inc., 1986.

Cheney D., "Genetic Manipulation of Marine Algae by Protoplast Fusion" Proceedings of the First Int'l Symposium on Marine Molecular Biology Oct. 9-11, 1988, Baltimore, Md.

Kapraun, D. F. and D. W. Freshwater, "Cell Isolation, Parasexual Hybridization and Strain Selection in Ulvaria oxysperma (Kuetz.) Blid. for Mariculture", Proceedings of the American Society for Cell Biology, 1988, Bethesda, Md.

Saga, Naotsune, Mariam Polne-Fuller and Aharon Gibor, "Protoplasts from Sea Weeds: Production and Fusion", Marine Science Institute and Dept. of Biological Sciences, UCSB, Calif., 1986.

Sharp, William R. and David A. Evans and Philip V. Ammirato, "Plant Genetic Engineering: Designing Crops to Meet Food Industry Specifications" Food Technology, Feb., 1984.

Van der Meer, John P., "Genetics of Gracilaria sp. (Rhodophyceae, Gigartinales) III. Non-Mendelian gene transmission", Phycologia 17(3), 314-318 (1978).

World Patents Index, Abstract of Japanese patent 64-74980 (1989).

Donald F. Kapraun, "Recovery and development of parasexual fusion products in Enteromorpha linza (L.) J. Ag. (Uvales, Chlorophyta)" in J. of Appl. Phycology I, p. 239-246, 1989.

METHODS FOR PRODUCING IMPROVED STRAINS OF SEAWEED BY FUSION OF SPORE-PROTOPLASTS, AND RESULTANT SEAWEEDS AND PHYCOCOLLOIDS

This application is a continuation of application Ser. No. 07/815,641, filed Dec. 30, 1991, now abandoned, which is a continuation of application Ser. No. 07/395,445, filed Aug. 17, 1989, now abandoned.

FIELD OF THE INVENTION

This invention pertains to marine algae, and more particularly, to methods for producing improved seaweed strains by genetic manipulation and genetic engineering.

BACKGROUND OF THE INVENTION

Phycocolloids are natural gums produced by and extracted from marine algae. The three principal types of commercially valuable phycocolloids are agar, carrageenan and alginate. Agar and carrageenan are polysaccharides produced in the cell walls of certain red algae or Rhodophyta, while alginate is a cell wall component of certain brown algae or Phaeophyta. Together, these three groups of phycocolloids form the basis for a seaweed processing industry worth several hundred million dollars annually.

Traditionally, the raw materials for agar, carrageenan and alginate have come from harvests of wild populations of marine algae. In recent years, certain types of carrageenan and alginate-producing seaweeds have been cultivated in the Pacific basin, the raw material for carrageenan being produced in the Philippines and Indonesia, and that for alginate in China. However, due to overharvesting of wild populations and increasing demand for products, current supplies of high-quality agar and certain types of carrageenan are insufficient to meet the seaweed processing industry's needs. There is therefore great interest in developing methods for cultivating agar seaweeds, and in expanding cultivation of certain carrageenan seaweeds. In addition, the industry desires new varieties of carrageenan and agar, which are not apparently found in wild plants.

To meet these present and future needs of the seaweed processing and phycocolloid industry, it is necessary to develop genetically improved strains of seaweed which would provide such new products as well as advantageous cultivation properties.

In the past, most seaweed strain improvement efforts have been restricted to the use of classical plant breeding techniques such as strain selection, mutagenesis, and sexual hybridization. Such efforts have produced very few new and commercially valuable strains of seaweeds.

To date, no new and valuable strains of agar- or carrageenan-producing red algae have been produced in the laboratory, primarily because efficient and effective means for producing such strains have not been available. The plant strains currently used in carrageenan cultivation were developed by application of tedious traditional strain selection procedures.

An important traditional method for development of new and improved strains of land plant crop species is sexual hybridization. This has generally involved sexual crossing of closely-related but often different species to produce a hybrid plant that shows hybrid vigor or heterosis. Common agricultural examples include hybrid corn and wheat.

Compared to its important role in land plant crop improvement, application of sexual hybridization to seaweed strain improvement has been extremely limited, especially in red algae. This is due in part to difficulties in obtaining the necessary plants of both sexes of both species. For example, in some carrageenophytes such as Eucheuma, the principal carrageenophyte cultivated, male plants are rare, and in some species, unknown. Furthermore, red algae also appear to lack interspecific interfertility.

Both intraspecific and interspecific crosses in carrageenan-producing red algae have so far failed to yield viable hybrids. For example, efforts to cross different populations of the same species in Chondrus (Chen and Taylor, Botanica Mar., 23, 441–448 (1980)), and in Gigartina (Guiry and West, J. Phycol., 19, 474–494 (1983)), have been unsuccessful in producing fertile hybrid progeny.

Attempts to cross several different species of Gracilaria, the major source of raw material for agar, have also failed. In each case, populations of different Gracilaria species appeared to be incompatible and could not be sexually crossed (e.g., Bird and McLachlan, Botanica Mar., 25, 557–562 (1982); Plastino and De Oliveira, Br. Phycol. J., 23, 267–271 (1988)). Thus, it appears that interspecific sexual hybridization is extremely limited or impossible in the red algae, presumably because of strict incompatibility barriers between species.

Similar incompatibility barriers apparently do not exist in the brown algae, as there are several reports of sexual hybridization between different species. However, in all cases these hybrids have proven to be nonviable or unable to produce progeny. Thus, it appears that sexual hybridization is not a practical method for strain improvement in brown or red algae. New strain improvement techniques are needed for such algae.

Protoplast fusion techniques have been applied to land plants to produce somatic hybrids. These techniques do not require sexual hybridization and so can produce hybrids between two plants of the same or different species regardless of their sexual compatability.

Protoplast fusion has been attempted in several marine algae, but has thus far failed to produce somatic hybrids. A major cause for this failure has been the inability of researchers to regenerate whole plants from the fusion products. Saga, et al, Beihefte zur Nova Hedwigia, 83, 37–43 (1986), have reported an attempt to fuse protoplasts from a green alga, Enteromorpha, with those from Porphyra, a red alga. A heterokaryon or fusion product was apparently formed, but the authors were unable to regenerate whole plants. Protoplast regeneration in general has been accomplished in only a few genera of non-commercial, non-phycocolloid-producing seaweeds to date. Similar efforts to regenerate plants from protoplasts of commercial phycocolloid-producing seaweeds have failed. For example, Cheney, et al., J. Phycol., 22, 238 (1986), describe methods for producing protoplasts in the agarophyte Gracilaria, but were unable to regenerate whole plants from these protoplasts. Likewise, it has not been possible to regenerate protoplasts from carrageenan-producing red seaweeds, or from alginate-producing brown seaweeds into whole plants. Kloareg, et al., Plant Sci., in press, 1989) report isolation of large numbers of protoplasts from the brown alga Macrocystis, but attempts to regenerate whole plants from the protoplasts were unsuccessful.

Successful protoplast fusion and regeneration have been reported in only one genus of seaweed to date, Porphyra, a red seaweed which is known to have excellent regenerative capabilities. Fujita and Mijita, Jap. J. Phycol., 35, 201 (1987), reported regeneration of whole plants from protoplast fusion products of Porphyra, but the resultant plants were chimeras, not true genomic hybrids. As the DNA of the parental plants remains segregated in a chimeric plant, such plants are not the same as hybrids and do not provide the benefits of a hybrid. Thus, chimeras have little or no commercial value for the production of phycocolloids.

Thus, efforts to develop improved strains of phycocolloid-producing marine algae have been frustrated by the inability to apply to red and brown seaweeds currently-used techniques which are applicable to land plants. Sexual hybridization fails because of incompatibility barriers. Somatic hybridization through protoplast fusion fails because protoplasts either cannot be regenerated to whole plants or do not produce true hybrids. In addition, it should be noted that recombinant DNA gene transformation methods (e.g., direct DNA uptake, microinjection) cannot be applied to marine algae because such methods are normally used in conjunction with protoplasts, and protoplasts in phycocolloid-producing marine algae cannot currently be regenerated to whole plants. New and improved methods which allow for successful protoplast fusion and regeneration as well as application of recombinant DNA gene transformation techniques are clearly needed if improved strains of phycocolloid-producing marine algae are to be produced.

SUMMARY

The present invention provides two routes to genetically improved marine algae, thus for the first time permitting commercially important seaweeds to be modified conveniently to achieve new and improved properties and phycocolloid products.

The first step in both processes involves preparing protoplasts from spores of one or more selected parent algal plants. In contrast to protoplasts from vegetative algal cells, such spore-protoplasts have been found to be capable of undergoing protoplast fusion to form true hybrids (heterokaryons), and that these hybrid fusion products can be regenerated into whole plants. Spore-protoplasts can also accept foreign DNA to form transformed spore-protoplasts which can similarly be regenerated into whole plants.

A process for producing hybrid marine algae includes the steps of preparing protoplasts from spores of two parental algal plants; fusing the resulting spore-protoplasts to form heterokaryon fusion products; isolating selected fusion products produced in the fusing step; and culturing these fusion products to produce multicellular material.

Hybrid marine algae are produced by the above-described process involving fusion of spore-protoplasts. They possess at least one property different in kind or degree from properties of presently known hybrid algae. The process of the invention produces hybrids which cannot at present be produced by sexual hybridization.

A process for producing phycocolloids includes the steps of the process for producing hybrid marine algae, as well as the additional steps of processing the hybrid multicellular material to recover phycocolloids. Phycocolloids produced by this process may be new materials possessing at least one property different in kind or degree of presently known phycocolloids.

Similarly, a process for producing transgenic marine algae includes the steps of preparing protoplasts from spores of a marine algal plant; introducing foreign DNA into these spore-protoplasts to form transformed spore-protoplasts; selecting transformed spore-protoplasts; and culturing the selected transformed spore-protoplasts to produce transgenic multicellular material.

Transgenic marine algae are produced by the above-described process involving introduction of foreign DNA into spore-protoplasts. These are new plants which possess at least one property different in kind or degree from properties of presently known algae.

A second process for producing phycocolloids includes the steps of the process for producing transgenic marine algae as well as additional step of processing the transgenic multicellular material to recover phycocolloids. Phycocolloids produced by this process may be new materials possessing at least one property different in kind or degree from properties of presently known phycocolloids.

BRIEF DESCRIPTION OF THE DRAWING

The invention will be more completely understood from a consideration of the following detailed description taken in conjunction with the drawing, in which.

DETAILED DESCRIPTION OF THE INVENTION

Figure 1:
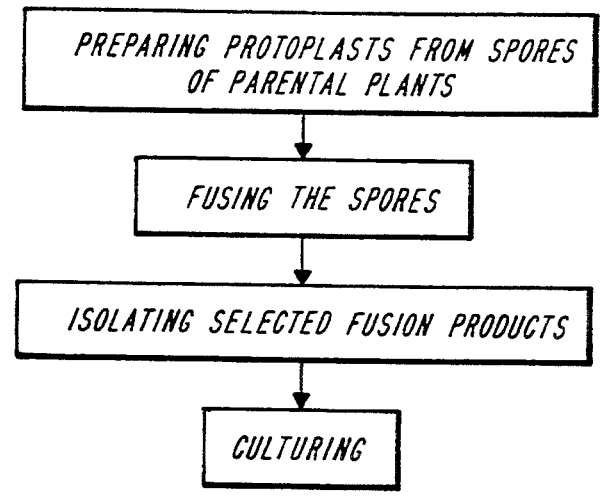
FIG. 1 shows a flow chart of the method for forming hybrids of marine algae.
Figure 2:
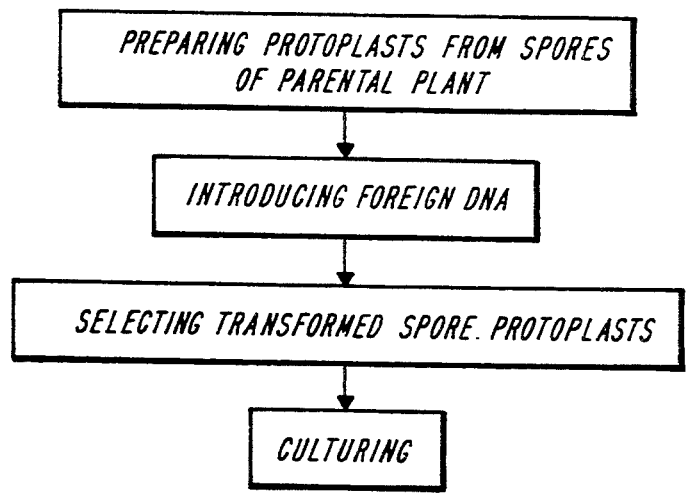
FIG. 2 shows a flow chart of the method for producing genetically modified marine algae.

The present invention relates to methods for genetically manipulating or engineering commercially valuable phycocolloid-producing seaweeds, for strain improvement in such marine algae. These methods are particularly applicable to red seaweeds that produce the phycocolloids carrageenan or agar.

One method involves fusion of spore-protoplasts to produce somatic hybrids. Because somatic hybridization is an alternative to sexual hybridization which does not require sexual compatibility or interfertility, new genetic variants or hybrids are produced which would not occur in nature. Such hybrids possess combinations of the genetic material found in the respective parental species, and therefore are expected to exhibit combinations of their traits.

A second method for strain improvement of marine algae involves introduction of foreign DNA into spore-protoplasts by application of gene transfer methods. Foreign DNA refers to DNA derived from a species other than the recipient organism's species and consists of a portion of DNA containing one or more genes. The products of such gene transfers could thus possess traits found in other species of marine algae or unrelated organisms.

The methods of the invention include a number of improvements over the prior art, which allow genetic engineering and manipulation techniques to be applied to phycocolloid-producing marine algae. One such is improvement the use of spore-protoplasts for protoplast fusion or as recipients of foreign DNA. The term spore-protoplast, as used herein, refers to any spore-derived protoplast, the term protoplast meaning a plant cell from which the cell wall has been removed. We have found that spore-protoplasts can be fused and regenerated to whole plants, in contrast to protoplasts derived from vegetative cells of the plants, which either cannot be regenerated or upon regeneration produce chimeras rather than the desired hybrids.

Spore-Protoplast Fusion and Somatic Hybridization

A) Species Selection

The parental species selected for fusion are chosen on the basis of traits they possess which it would be advantageous or commercially-desirable to combine. Based on evidence from protoplast fusion in land plants, where protoplast fusions have been completed between plants that were intraspecific, interspecific and even intergeneric, the two parental plants do not have to belong to the same species. Our evidence suggests that spore-protoplasts from marine algae behave similarly. Thus, one can select two different species of algae for hybridization, for example, one species having advantageous cultivation properties and the other species producing phycocolloids with desirable properties.

As an example of such a hybridization, a somatic hybrid between two different species of the agarophyte Gracilaria which cannot be sexually hybridized, *G. tikvahiae* and *G. chilensis*, was prepared by the spore-protoplast fusion method of the invention. These species were selected because each possesses desirable properties not found in the other. *Gracilaria tikvahiae* is a fast-growing species with proven cultivation capability but produces poor quality agar. *Gracilaria chilensis* produces a high quality, commercially valuable agar, but has a growth rate and habitat preference that make it difficult to cultivate. It was hoped that a hybrid between the two might exhibit both valuable traits found in the parental species, fast growth and high quality agar. The experiment, described in detail below, shows that the spore-protoplast fusion of the invention produces true somatic hybrids of different and incompatible species of algae.

Typical examples of the macroscopic marine algal organisms to which the invention can be applied include those species which are or could be used by the phycocolloid industry as sources of raw material for kappa, iota, lambda and beta carrageenan, as well as for agar and agarose. Examples include the various species of *Eucheuma, Chondrus, Gigartina, Hypnea,* and *Iridaea* for carrageenan, and species of *Gracilaria, Pterocladia* and *Gelidium* for agar.

After the two parental species are selected for fusion, particular strains of each are chosen based upon features such as ploidy level and/or possession of a marker that can be used in hybrid selection. A variety of fusions is possible in marine algae between spore-protoplasts of similar or different ploidy levels. In red algae, for example, haploid tetraspores produced by tetrasporic plants would allow diploid hybrids to be produced. Similarly, diploid carpospores produced by carposporic plants can be fused with haploid tetraspores to produce triploids or fused with themselves to produce tetraploids.

Another consideration in selecting particular strains for fusion is whether they have particular traits that would facilitate hybrid selection following fusion. One such trait is differential pigmentation. Use of parental plants with different pigmentation allows easy recognition and isolation of heterokaryons. The term heterokaryon refers to a fusion product derived from different parental cells, in contrast to a homokaryon which is produced from a somatic fusion between cells of the same parental cell line. It is important in a somatic fusion to have some mechanism by which heterokaryons can be distinguished and isolated from the homokaryons and unfused cells following fusion. In the experiment with the red alga Gracilaria described in detail below, two differentially-pigmented parental strains were selected for fusion- one that is a red pigmented wild-type, and one that is a green-pigmented mutant. If two differentially-pigmented strains are not available, tagging reagents known to those skilled in the art, such as the fluorochrome stain fluorescein diacetate (FDA), can be used to "label" or tag one type of protoplast prior to fusion. Both types of marker can be used to distinguish heterokaryons as described below in section E.

B) Spore Production

As explained above, an important feature of this invention is use of spores, from which protoplasts are derived for fusion or introduction of foreign DNA. We have found that such spores offer the advantage that protoplasts derived from them possess generally consistently high regeneration capability that is lacking in protoplasts produced from vegetative tissue of marine algae.

Sporulating plants of the two selected parental species are cultured using methods known in the art, such that both plant types will simultaneously release large numbers of the spores desired. The specific methods used to culture plants and induce spore release vary from species to species and the type of spores desired. However, culturing generally involves such steps as establishing epiphyte-free and axenic or essentially bacteria-free cultures, culturing the plants under conditions that are optimal for growth followed by a period under suboptimal conditions, and optionally, a return to optimal growth conditions. Optimal and suboptimal growth conditions, including culture medium, temperature, and irradiance vary from species to species. Generally, changes in culture conditions (e.g., a reduction in nutrient levels followed by normal nutrient levels) appear responsible for spore release. There are a number of reports in the scientific literature describing the specific conditions for inducing spore release in various marine algae.

C) Spore-Protoplast Production

The term spore-protoplast refers to protoplasts derived from spores, which in the case of red algae are of two types, tetraspores and carpospores, and in the case of brown algae are of one type, zoospores. In general, spores are single cells that marine algae produce for asexual reproduction and which, upon release, are able to attach to the substratum and quickly divide and develop into new plants. Although basically similar to protoplasts produced from vegetative cells, spore protoplasts appear to be generally more cytoplasmically dense and have a smaller vacuole.

Although spores may lack a cell wall when they are first released, and therefore could be technically considered protoplasts, they usually form a cell wall very quickly, e.g., within 24 hours. During this time of cell wall formation, as well as after cell wall formation, we have found it impossible to obtain successful fusion employing spores. Instead, we have found that the preferred method for fusion requires use of protoplasts produced from spores. Although such may be produced by the inhibition of cell wall formation in freshly released spores, this can have subsequent damaging effects.

The preferred method for producing spore-protoplasts is by treating spores with an enzyme mixture designed to digest their cell walls without substantially and adversely affecting the viability and regeneration capability of the resultant spore-protoplasts. The particular enzyme mixture used to digest the cell wall of any marine alga depends upon the biochemical composition of its cell wall. Enzyme mixtures have been described for the production of protoplasts for approximately 20 species of marine algae, including the agar-producing red alga, Gracilaria. In this regard, see Cheney et al., J. Phyco., 22, 238–243, (1986).

The enzyme mixture used to produce spore-protoplasts from Gracilaria in the present invention is preferred over that described in the reference above, and contains only two enzymes, Onozuka RS cellulase and agarase, instead of the original four enzymes. The reduced enzyme composition provided improved protoplast viability and regeneration, without greatly affecting yield. The production of spore-protoplasts in other marine algae may, of course, require a different enzyme treatment.

D) Spore-Protoplast Fusion

Spore-protoplasts are fused using the same basic methods of fusion that are applied for fusing protoplasts from vegetative cells. The two methods most widely used with land plants today are chemical fusion and electrofusion. Both fusion methods are applicable in the present invention. However, the method of preference is chemical fusion.

In general, the fusion of spore-protoplasts is accomplished by treating the protoplasts with a solution of a chemical fusogen to cause them to agglutinate, treating the agglutinated spore-protoplasts with a hypotonic calcium-containing elution (fusion) solution which is effective to cause them to fuse, replacing the elution solution with a hypertonic calcium-containing washing solution to remove fusogen residues and provide a hypertonic environment, and finally replacing the washing solution with culture medium which is effective to stimulate cell wall formation and cell division. Examples of fusogens which are expected to function in this invention are polyethylene glycol, sodium nitrate, dextran, high pH (basic) calcium-containing solutions, and combinations of these.

Spore-protoplasts of marine algae such as Gracilaria are effectively fused using the chemical fusogen polyethylene glycol (PEG) and a low Ca-high pH elution (fusion) step following protoplast agglutination. While the basic methods are somewhat similar to those first used by Kao and Michayluk (Planta, 115, 355–367, 1974) with land plants and, more recently, by Saga et al. (Beihefte zur Nova Hedwigia, 83, 37–43, 1986) with marine algae, several differences are important in the present invention. These include, in addition to the use of spore-protoplasts, the use of a high molecular weight (e.g., 4000–6000 Dalton) low carbonyl content PEG, the use of a lower calcium concentration in the elution (fusion) medium, the replacement of the elution (fusion) medium with a washing medium, and a step-wise addition of culture medium directly to the culture dish in which protoplasts are fused. Regarding the carbonyl content of the PEG, it has been reported by Chand (1989) that PEG having relatively high carbonyl contents causes protoplast fusion products to exhibit poor viability, best results being obtained with PEG having relatively low carbonyl content. In addition, methods for isolating and culturing putative heterokaryons are also described which are an improvement over the prior art.

In general, equal numbers of spore-protoplasts from the two parents are gently mixed together and fused as soon after they are produced as possible. For best results, the combined concentration of protoplasts should be great enough to insure a close proximity of protoplasts in the "fusion drops" (e.g., $2.5-5 \times 10$ protoplasts per ml). If the spore-protoplasts are produced from non-axenic parental plants, subsequent bacterial contamination during culture can be reduced by using purification procedures such as a Percoll density gradient method known to the art.

The steps of the fusion process are as follows:

1. A small number (e.g., 3 or 4) of drops of the spore-protoplast mixture are pipetted into the center of a culture dish which has a coated surface. Nunc culture dishes (3.5 cm diameter) are preferred. The protoplast "drop" is then left undisturbed for a brief period to allow the protoplasts to settle.

2. Next, an approximately equal number of drops of a 0–50% solution of high molecular weight low carbonyl content PEG (e.g., Kochlight 6000) are added to the periphery of the large central drop of protoplasts. The PEG should be made up fresh just before use and filter sterilized. This mixture is left undisturbed for 30–90 minutes, or until protoplast agglutination occurs.

3. Once protoplast agglutination has occurred, the PEG solution is diluted and replaced preferably with a low calcium-high pH elution (fusion) solution. The elution (fusion) solution of preference contains sea water plus 5–40 (preferably 5–10) millimolar calcium, has a pH of 8–9, and is hypotonic relative to the PEG solution. Several drops (approximately equal to the number of drops of PEG solution added) of this solution are added dropwise to the periphery and top of the PEG-protoplast mixture. After a few minutes, a number of drops equal to the drops of added solution are removed by pipet, and fresh drops of the elution solution are again added, as before. After a total of approximately 10–20 minutes, the protoplast mixtures are carefully examined with an inverted microscope for the presence of fusion products. If fusion products have been produced, one proceeds to step four; if not, additional drops of PEG solution are added and steps two and three are repeated.

4. After fusion products have been produced, it is important to begin removing the elution (fusion) solution and adding a washing solution as quickly as possible. The washing solution is similar to the protoplast culture medium used, except that it generally has a higher concentration of calcium, and also a higher osmolarity (i.e., it is more hypertonic). The washing solution is added, several drops at a time, to the periphery of the protoplast mixture. After a few minutes (e.g., 3–5 min.), a number of drops equal to the original addition are removed by piper from the periphery, being careful not to disturb the protoplasts. This procedure is repeated several times over a 20–40 minute period.

5. Once it is concluded that all of the elution solution has been replaced by the washing solution, culture medium is added gradually, while at the same time removing the washing solution until it is concluded that all of the washing solution has been replaced.

Subsequently, the dish is slowly flooded with culture medium, being careful not to disturb the protoplasts. The culture medium used should be one that has been pretested and proven successful in spore-protoplast regeneration. The optimal culture medium and conditions will vary depending upon the species. However, in general, it appears preferable to culture the products of spore-protoplast fusion in a slightly hypertonic seawater medium containing a low concentration of added calcium, under relatively low light conditions.

E) Isolation and Culture of Heterokaryons

In any fusion experiment, it is important to have a reliable method for identifying and isolating cells that are potential hybrids or heterokaryons (i.e., biparental fusion products) from homokaryons (i.e., uniparental fusion products) and unfused protoplasts. Various methods have been described for identifying heterokaryons. See the publication by Harms in "Plant Protoplasts" edited by Fowke and Constabel, pp 169-203, CRC Press (1985).

One of the simplest methods for identifying heterokaryons is the use of visual markers, such as those which exhibit a combination of pigments or plastid type found in the parental plants. For example, fusions of spore-protoplasts from red-pigmented and green-pigmented plants produced heterokaryons which were easily distinguished by their red and green, bicolor chloroplast composition. Alternatively, heterokaryons may be identified with the use of fluorescent stains. Generally, this involves staining one of the parental cell types with a fluorescent dye like FDA (which stains cells yellowish) and looking for heterokaryons that exhibit dual fluorescence, that is, both FDA fluorescence and normal chlorophyll autofluorescence (which is reddish).

Heterokaryons that can be visually distinguished, however, may lose their distinctive appearance within a relatively short period of time. Heterokaryon cells with two different types of chloroplasts tend to lose one or the other chloroplast type within 1-2 weeks after fusion, apparently due to cytoplasmic incompatibility. Therefore, it is essential to isolate the heterokaryon cells from the homokaryon and unfused cells while they are still easily distinguished.

A preferred method for isolating heterokaryon cells is to use microisolation (micromanipulation) techniques to transfer them to a new culture dish. Such techniques allow for the mechanical isolation and transfer of essentially single cells from one culture dish to another. The specific methods involved have been described and are known to the art. An alternative method is to "mark" the location of heterokaryons in the fusion dish itself with nearby scratches made by a micropipet; this allows for easy subsequent relocation of heterokaryons.

Once isolated from the protoplast fusion dish, heterokaryon cells are cultured under conditions that will both stimulate their growth and allow for their easy identification. This is generally done by first culturing the fusion product cells with other healthy, dividing cells or callus which can act as a nurse culture until the fusion cells have developed into cell colonies. These colonies are then transferred into a second culture condition which is effective to produce and maintain the multicellular material as an undifferentiated cell mass lacking an organized meristem, or as a whole plant. Preferably the second culture is effective to promote whole plant regeneration and growth.

A preferred procedure is to use a so-called nurse culture composed of cell colonies or callus derived from one of the parental species used in the fusion. By using cell colonies or callus that are of different pigmentation and/or morphology than the heterokaryon, the ability to distinguish heterokaryons after development is maintained. Previously it has been difficult to produce and grow callus in liquid culture of most phycocolloid-producing marine algae and has been impossible in some cases, for example, Gracilaria. In the present invention, the preferred nurse culture consists of callus-like red-pigmented cell colonies which we have found can be induced and maintained by the application of certain antibiotics to cells of one or both parental plants. For example, through the use of certain antibiotics we have produced callus-like cell colonies in *G. chilensis* which are easily distinguished from the more normal, non-callus-like development of *G. tikvahiae* cell colonies. Such callus-like cell colonies are produced by culturing single marine algal cells of *G. chilensis* (e.g., spores) in medium containing at least one antibiotic capable of inducing callus formation, the concentration of antibiotic being effective to induce callus formation and maintain the resulting callus, but not so high that the cells are killed. Typical concentrations of antibiotic found to be useful for this purpose are in the range of about 50 to 150 micrograms per milliliter. We have found that the antibiotics chloramphenicol and chlorotetracycline function for this purpose. The use of such antibiotics to induce callus for a nurse culture in marine algae is novel.

Heterokaryons are maintained in the nurse culture until they have developed to a multicellular colony stage. At this point they are transferred to a flask on a shaker or to an aerated flask, whichever promotes their most rapid development into whole plants. The whole plants produced from the heterokaryons isolated originally from the fusion dish should be considered as only putative hybrids. It is essential that their hybrid nature be confirmed. This is generally done by demonstrating that gene products are produced by the putative hybrid which are encoded by the genomes of both parental material. The preferred method for doing this is to use electrophoretic banding patterns of specific isoenzymes. Another approach is to use restriction fragment length polymorphism fingerprinting or species specific DNA-clone probes to demonstrate hybrids. Both methods can unequivocally prove hybridity, whereas other methods, such as morphology, chromosome number and total amount of DNA, do not.

Hybrid algal plants of the invention will generally differ from presently existing algae in their biochemical and/or cultivation-related properties. At least some phycocolloids produced by these hybrid algae are expected to differ from known phycocolloids in their gelling or viscosity characteristics.

Foreign Gene Transfer

Gene transfer by somatic hybridization results in the transfer of generally more than one gene. Sometimes it is desirable to transfer only limited, perhaps single, genetic attributes from a donor to a recipient species. In land plants this is done currently by use of various foreign DNA transfer methods, including Agrobacterium-mediated gene transfer, microinjection, or by direct DNA uptake methods. Each method basically consists of introducing small fragments of DNA into either a plant cell or protoplast, such that the DNA becomes incorporated into the host cell's chromosomes. The plants subsequently derived from such cells are said to be "transformed" and are called "transgenic plants".

In the past, these gene transfer methods could not be successfully applied to marine algae because of either host-plant restrictions (in the case of Agrobacterium-mediated gene transfer) or inability to regenerate protoplasts. In the present invention, these gene transfer methods are applicable to marine algae through the use of spore-protoplasts.

One of the most widely used approaches to foreign gene transfer is the use of Agrobacterium tumafaciens as a vector system. Agrobacterium tumefaciens is a land plant pathogen that is able to transfer genes encoded in the T-DNA region of its Ti-plasmid into plant cells at a site of wounding. The general method is well described in the literature (e.g. Power et al., Methods in Enzymology, 118, 578–594, 1986). It has been modified in a variety of ways in order to be applied to a broader range of plant species including some that are not natural hosts of Agrobacterium. See, for example, Chand et al., Plant Cell Reports, 8, 86–89 (1989). In the present invention, Agrobacterium tumefaciens containing the foreign gene of interest can be either co-cultured with spore-protoplasts that have partially regenerated cell walls or electroporated with freshly isolated spore-protoplasts as described by Chand, et al. Generally, a disarmed, or non-disease causing, strain of Agrobacterium tumefaciens is utilized, and the gene of interest is linked within the T-DNA region of the Ti-plasmid to a marker gene conferring resistance to an antibiotic that can be used for selecting transformants. Since all the genes within the T-DNA borders are transferred, cells expressing antibiotic resistance would be expected to also contain any other genes that had been engineered into the T-DNA region. The methods of spore-protoplast production are the same as described above for fusion. The detailed methods for preparation of the Ti-plasmid and Agrobacterium strains are described in the literature.

A second commonly used approach for gene transfer in land plants involves the direct introduction of purified DNA into protoplasts. The three basic methods for direct gene transfer include: 1) polyethylene glycol (PEG)-mediated DNA uptake, 2) electroporation-mediated DNA uptake and 3) microinjection. While such methods have proven successful with a variety of land plants, they have not been applicable to the marine algae of interest because of restrictions in regenerating whole plants from protoplasts. In the present invention, spore-protoplasts are used as recipients of the foreign DNA. The methods of spore-protoplast production are the same as described above for fusion. Specific methods for each of the gene transfer methods listed are described in the literature. See, for example, Vasil et al., Plant Cell Reports, 7, 499–503 (1988).

In the method of the invention involving foreign gene transfer, the spore-protoplasts are produced in the same manner as discussed above with respect to protoplast fusion. Likewise the transformed spore protoplasts are cultured in the same manner as discussed with respect to the above-described protoplast fusion products. As with the protoplast fusion method, the final products may be undifferentiated cells, a multicellular colony without an organized meristem, or a whole plant.

The methods of the invention are generally applicable to marine algae, particularly the red and brown algae. Red algae include the genera Gracilaria, Eucheuma, Chondrus, Gigartina, Iridaea, Pterocladia, Hypnea and Gelidium. Brown algae include the genera Laminaria, Macrocystis, Ecklonia, Nereocystis, Durvillea, Lessonia, and Sargassum.

The following examples are included for illustrative purposes only and are not intended to limit the scope of this invention.

EXAMPLE 1

The following example describes the production of a somatic hybrid between two non-interfertile species of Gracilaria, *G. tikvahiae* and *G. chilensis*. Somatic hybridization was accomplished by fusing protoplasts produced from tetraspores (spore-protoplasts) released by fertile, tetrasporic (tetrasporophytic) plants of each species. The particular strain of each species used in this example included a green-pigmented mutant strain of *G. tikvahiae* designated NMG and isolated by John van der Meer, as described in Phycologia 17, 314–318 (1978), and a wild-type, red-pigmented strain of *G. chilensis* from central Chile.

Stock cultures of parental plants were established from plant tips that had been cleaned of all epiphytes and treated with a betadine solution (1% for 2 min) followed by an antibiotic solution designated E3 (consisting of 30 $\mu$g/ml each of polymixin B, nalidixic acid, erythromycin, colisin, vancomycin, ampicillin, trimethoprin and chlorotetracycline) prior to being grown in aerated flasks. Parental plant stock cultures were maintained in ESS enriched seawater medium (described in Bradley, et al., Plant Cell Tissue and Organ Culture, 12, 55–60 (1988)) changed every 7 days, at a 12:12 light-:dark photoperiod and an irradiance of 70$\mu$ Einstein.

Prior to a fusion experiment, plants that showed signs of tetrasporangial maturity, determined by microscopic examination or by the presence of spores on the bottom of the culture flask itself, were removed from the flasks. They were cleaned with a small artist's brush and transferred to petri dishes containing fresh ESS media. These culture dishes were checked daily for spore release. Spores were collected on the third day after being transferred to fresh ESS media. They were collected by piper after being concentrated in the center of the dish using a gentle swirling motion and placed in a sterile screw-cap 15 ml centrifuge tube. These spores were further concentrated to a 0.5 ml. pellet by gentle centrifugation consisting of 6 min at 700 rpm ($\neq$80$\times$g) with a bench top centrifuge. Spores of each parental strain were initially collected separately and adjusted so that the concentration of each was approximately equal. Then the two pellets were combined into a single centrifuge tube, rinsed with added ESS media and recentrifuged to form a final pellet of 0.5 ml.

The 0.5 ml combined pellet of parental spores was suspended in 3 ml of an enzyme mixture in a 3.5 cm Nunc culture dish. The enzyme mixture used was made up in 20 ml batches and consisted of 1% Onozuka RS, 5 bottles (5,000 units each) of agarase from Calbiochem, 1.0 m mannitol, 0.2% BSA, in 60% half-strength ESS and 40% distilled water and pH adjusted to 6.8. This mixture was stirred for 1 hour, then filter sterilized with a 0.2$\mu$ filter and stored in the freezer until use. During enzyme incubation, the Nunc dish was covered with aluminum foil and gently shaken on an orbital shaker at 30 rpm for 4.75 hr at a temperature of 28° C.

Following enzyme incubation, the contents of the Nunc dish were gently pipetted on top of a freshly prepared 25% Percoll rinse solution (consisting of 25% Percoll) in a sterile, screw-cap 15 ml centrifuge tube. The protoplasts were initially collected by centrifuging at 700 rpm (80×g) for 6 minutes, and were then resuspended and re-centrifuged twice in rinse solution at 600 rpm (70×g) for 5 minutes. The rinse solution consisted of 0.9M mannitol and 5 mM CaCl in 50% half-strength ESS plus 50% distilled water at a pH adjusted to 6.8. The rinse solution was made up fresh. After the final centrifugation, the supernatant was removed to leave a protoplast pellet of 0.5 ml. with a protoplast density approximately 2×10 protoplasts per ml.

The protoplast pellet was gently resuspended in the centrifuge tube by piper and then transferred to the center of three 3.5 cm Nunc culture dishes, three drops (approximately 150 μl) per dish. These were left undisturbed for approximately 15 minutes to allow the protoplasts to settle, after which 4 drops of PEG agglutination solution were added to opposite sides of the large central "drop" of protoplasts. The PEG agglutination solution was freshly prepared and contained 40% Kocklight 6000 polyethylene glycol in distilled water plus either 0.4M or 0.3M mannitol and 25 mM $CaCl_2$. Other PEG solutions containing 0.25M NaCl and 50 mM $CaCl_2$ did not prove as satisfactory. The PEG solution and all subsequent solutions were filter sterilized using a 0.2μ filter.

Forty-five minutes after adding PEG, 4 drops of elution (fusion) solution were carefully removed from the central "drop" of protoplasts and 4 more drops of PEG agglutination solution were added. After another 20 minutes, 4 drops of fusion solution were added slowly to the top of the "drop" of protoplasts. The fusion solution contained half-strength ESS, plus 36 mM $CaCl_2$, 0.05M glycine, 0.1M mannitol adjusted to pH 9.1 with NaOH and KOH. Five minutes later, 4 more drops were removed and replaced with fusion solution. At this point, protoplast fusions were observed by direct microscopic observation with an inverted microscope.

Approximately 1 hour after adding fusion solution, a washing solution was added gradually by adding and removing several drops at a time. In subsequent experiments it proved beneficial to add washing solution at an earlier time, e.g., 10-30 minutes after adding fusion solution. The washing solution contained three-quarters strength ESS, plus 0.6M mannitol and 27.5 mM $CaCl_2$ at pH 7.6. Addition and removal of the wash solution were repeated several times over the next 25 minutes, after which a culture solution was gradually added in similar fashion to the washing solution. The culture solution contained 60% wash solution and 40% half-strength ESS, plus 0.4M mannitol and 12.5 mM $CaCl_2$ at a pH of 7.6. Finally, the culture dish was slowly flooded with culture solution, and carefully sealed with parafilm. The culture dishes were cultured in a clear plastic container to prevent desiccation in a growth chamber with 25μ Einstein/$m^2$/sec at Three days after fusion, dilution of the culture media was initiated by removing 1 ml of culture media from each dish and replacing it with 0.5 ml of ESS plus 2 drops of E3 antibiotic mixture. The culture media was again diluted 5 days after fusion by removing 0.5 ml of culture media and adding 0.5 ml of ESS plus 2 drops of E3. At this point, direct microscopic observations confirmed that red and green, bicolor heterokaryons observed earlier were still alive and healthy.

Eight days after fusion, attempts were made to either isolate heterokaryons to new culture dishes or "mark" them in their original culture dishes so that they could be easily relocated and checked for development. Several heterokaryons were transferred using a micropipet and micromanipulation equipment to a new culture dish containing a thin layer of 1% agarose on the bottom and ESS media. A better procedure was to simply "mark" the location of heterokaryons in the original dishes with scratches on the bottom of the dish caused by the micropiper. Fresh ESS medial plus 3 drops of E3 antibiotics were added weekly to all culture dishes.

The addition of the E3 antibiotics caused the red-pigmented, unfused cells of G. chilensis to produce callus-like growths after 3-5 weeks. After approximately 2 months, several putative hybrid cell colonies were isolated from the culture dishes and transferred to small (125 ml) aerated flasks for whole plant regeneration. These putative hybrid cell colonies were selected based upon unusual pigmentation-morphological characteristics they possessed. That is, they either exhibited green pigmentation and some callus-like growth (like that of G.chilensis) or were red-pigmented and did not exhibit callus-like growth (like G. tikvahiae). Isolated putative hybrid cell colonies were regenerated to whole plants in ESS media and cultured at 20° C., first at 25μ Einstein/$m^2$/sec and later at 70μ Einstein/$m^2$/sec. Upon whole plant development, these plants were tested for electrophoretic banding patterns of isoenzymes which would confirm hybridity using standard starch gel electrophoretic techniques as described in Cheney (see: Littler and Littler (eds.), Handbook of Phycological Methods: Ecological Field Methods, pp. 87-119, 1985), or with a modified starch-polyacrylamide gel as described in Cheney (submitted for publication in J. Phycol.). With staining for phosphoglucose isomerase (PGI), a hybrid, designated #18-HG2, has been identified by its possessing some bands of both parental species, G. tikvahiae and G. chilensis. #18-HG2 also possesses additional characteristics that provide evidence for its being a hybrid between G. tikvahiae and G. chilensis, including its production (although reduced) of tetraspores, and its being green-pigmented but having a very different branching pattern from that of G. tikvahiae. Other plants were identified which were not true hybrids (the product of biparental fusions) but were products of uniparental fusion, or homokaryons. The latter plants produced tetraspores in culture and therefore must possess a ploidy level of 2N or higher.

EXAMPLE 2

This example describes modifications to the techniques described in Example 1 which improve the yield and viability of heterokaryon production.

Spores and spore-protoplasts were prepared as described in Example 1, except that the enzyme treatment was reduced to 2.5-3 hours. Spore-protoplasts were fused similarly to that described except for using a PEG agglutination solution containing 50% Kochlight 6000 PEG in distilled water plus 0.4M mannitol and 5 mM $CaCl_2$, or an alternative PEG solution containing 50% Kochlight 6000 PEG in 50% ESS, 50% distilled water. Other modifications from Example 1 include the addition of a greater number of drops (6-8) of PEG agglutination solution only once to the "drop" of protoplasts. After 30-60 mins, a different Fusion solution was added which contained half-strength ESS plus 5 mM $CaCl_2$, 0.05M glycine, 0.1M mannitol, and 0.2% BSA adjusted to pH 9.0. An alternative Fusion solution used contained unenriched seawater, plus 10 mM $CaCl_2$, 0.05M glycine, 0.1% BSA, and 0.1M mannitol adjusted to pH 8.8. The washing and culturing steps were similar to those described in Example 1 except that the washing solution contained half-strength ESS instead of three-quarters strength ESS, and was added 10–30 minutes after the addition of the fusion solution. The culture solution contained half-strength ESS plus 12.5 mM $CaCl_2$, 0.2% BSA, and 0.4M mannitol at a pH of 7.1. The culture steps were similar to those in Example 1, except that in some cases heterokaryon cells and heterokaryon-derived cell colonies were transferred to new culture dishes without an agarose layer by micromanipulation and/or removal by sterile brush. These modifications increased the rate of heterokaryon production, and their survival.

EXAMPLE 3

This example describes techniques for the direct uptake of foreign DNA through the procedure of electroporation.

Spores and spore-protoplasts of *G. chilensis* were prepared similarly to the methods described in Example 1 except that a 2.5–3 hr enzyme treatment was used to produce spore-protoplasts instead of 4.75 hrs.

After enzyme treatment, the spore-protoplasts were first rinsed twice in the same rinse solution as described in Example 1, and then rinsed twice in an Electroporation Rinse solution, containing 100% distilled water plus 12.5 mM $CaCl_2$, 5 mM KCl, 12.5 mM NaCl, 0.7 m mannitol and 0.7 m sorbitol. After rinsing, the protoplasts density was adjusted to $1-2 \times 10^5$/ml. Protoplasts were electroporated in the chamber of a DIA-LOG electroporator using techniques similar to those described in Rech, et al., Protoplasma, 141, 169–176 (1987). Each protoplast sample consisted of 700 $\mu$l. The sample was incubated in the electropotation chamber with plasmid DNA (12.5 $\mu$g/ml) containing the chloramphenicol acetyltransferase (CAT) gene in the plasmid pCaM. Plasmid DNA was prepared using standard methods. See Fromm, et al., Proc. Natl. Acad. Sci., 82, 5824–5828 (1985).

Electroporation was conducted over a range of conditions, including voltages of 200–300 V/cm and pulses of 5.6–30 $\mu$sec., as well as single and multiple pulses. Immediately after electroporation, each sample was transferred to a 3.5 Nunc culture disk and was carefully flooded with the same Culture solution used in Example 1. Shortly after flooding with culture solution, 5 drops of a chloramphenical-containing antibiotic solution was added to each dish. This antibiotic solution contained 30 $\mu$g/ml each of Polymixin B, Erythromycin, Vancomycin, Ampicillin, Trimethoprin, and Gentamicin, plus 75 $\mu$g/ml of chloramphenicol.

Several of the electroporation treatments produced results that suggest that the CAT gene had been taken up the spore-protoplast. For example, a number of cells survived the antibiotic medium for a longer period than control-treated spore-protoplasts. However, these could not be tested for transient gene expression because of insufficient numbers, and could not be further tested for chloramphenicol resistance because of failure to survive to the cell colony stage. Modifications in the electroporation media and procedures should produce successful transformation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A process for producing hybrid marine red algae, comprising the following steps:

preparing protoplasts from spores of first and second parent red algal plants, both said first and second parent red algal plants being from the same genus, said genus being selected from the group consisting of the genera Gracilaria, Eucheuma, Chondrus, Gigartina, Iridaea, Pterocladia, Hypnea and Gelidium, and both said first and second parent red algal plants being from species that produce spores with either an agar or a carrageenan cell wall composition, said protoplasts being denominated first and second spore-protoplasts, respectively;

fusing said first and second spore-protoplasts to form heterokaryon fusion products;

isolating selected fusion products produced in said fusing step; and culturing said selected fusion products to produce multicellular material.

2. The process of claim 1, wherein said preparing step includes the step of treating spores of the first and second parental red algal plants with an enzyme mixture which is effective to digest their cell walls without substantially and adversely affecting the viability and regeneration capability of resultant spore-protoplasts.

3. The process of claim 1, wherein said fusing step includes the steps of treating said spore-protoplasts with a solution of a chemical fusogen effective to cause their agglutination;

treating the agglutinated spore-protoplasts with a hypotonic calcium-containing elution solution effective to cause them to fuse;

replacing said elution solution with hypertonic calcium-containing washing solution to remove elution solution and residues of said fusogen and provide a hypertonic environment; and replacing said washing solution with culture medium effective to stimulate cell wall formation and cell division.

4. The process of claim 3 wherein said chemical fusogen is selected from the group consisting of polyethylene glycol, sodium nitrate, dextran, a high-pH solution containing calcium ions, and combinations thereof which are effective to promote fusion.

5. The process of claim 1 wherein said fusing step includes electrofusion.

6. The process of claim 1 wherein said culturing step includes the steps of:

culturing isolated selected fusion product cells in a first culture in the presence of cells or callus derived from a marine red algal plant of the same genus as one of said parental red algal plants until said product fusion cells have developed into cell colonies; and transferring said cell colonies from said first culture into a second culture effective to promote whole plant regeneration and growth.

7. The process of claim 6 wherein said first culture comprises callus derived from one of said parent red algal plants.

8. The process of claim 1 wherein said multicellular material is an undifferentiated cell mass.

9. The process of claim 1 wherein said multicellular material is a whole plant.

10. A process for producing agar or carrageenan via hybrid marine red algae, comprising the following steps:

preparing protoplasts from spores of first and second parent red algal plants, both said first and second parent red algal plants being from the same genus, said genus being selected from the group consisting of the genera Gracilaria, Eucheuma, Chondrus, Gigartina, Iridaea, Pterocladia, Hypnea and Gelidium, and both said first and second parent red algal plants being from species that produce spores with either an agar or a carrageenan cell wall composition, said protoplasts being denominated first and second spore-protoplasts, respectively;

fusing said first and second spore-protoplasts, to from heterokaryon fusion products;

isolating selected fusion products produced in said fusing step;

culturing said selected fusion products to produce multicellular hybrid marine algal material; and processing said hybrid multicellular material to recover phycocolloid material.

* * * * *

UNITED STATES PATENT AND TRADEMARK OFFICE
CERTIFICATE OF CORRECTION

PATENT NO. : 5,426,040
DATED : June 20, 1995
INVENTOR(S) : Donald P. Cheney
Clifford Duke It is certified that error appears in the above-indentified patent and that said Letters Patent is hereby corrected as shown below:

Column 8, line 11, "2.5-5 X 10" should read --2.5-5 X $10^5$--.

Column 8, line 25, "0-50% solution" should read --40-50% solution--.

Column 8, line 64, "piper" should read --pipet--.

Column 12, line 44, "piper" should read --pipet--.

Column 12, line 48, "($\neq$80 X g)" should read --($\cong$80 X g)--.

Column 13, line 7, "CaCl" should read --$CaCl_2$--.

Column 13, line 12, "2 X 10" should read --2 X $10^5$--.

Column 13, line 14, "piper" should read --pipet--.

Column 13, line 59, "Einstein/$m^2$/sec at" should read --Einstein/$m^2$/sec at 20°C.--.

Column 14, line 10 and 11, "micropiper" should read --micropipet--.

Column 15, line 51, "chloramphenical-containing" should read --chloramphenicol-containing--.

UNITED STATES PATENT AND TRADEMARK OFFICE
CERTIFICATE OF CORRECTION

PATENT NO. : 5,426,040
DATED : June 20, 1995
INVENTOR(S) : Donald P. Cheney, et al It is certified that error appears in the above-identified patent and that said Letters Patent is hereby corrected as shown below:

Column 18, line 5, "from" should read --form--.

Signed and Sealed this

Third Day of November, 1998

Attest:

Attesting Officer

BRUCE LEHMAN

Commissioner of Patents and Trademarks